United States Patent [19]

Fukuura et al.

[11] Patent Number: 4,636,218
[45] Date of Patent: Jan. 13, 1987

[54] ARTIFICIAL ARTICULATION

[75] Inventors: Isamu Fukuura; Shigeo Niwa, both of Aichi, Japan

[73] Assignee: NGK Spark Plug Co., Ltd., Aichi, Japan

[21] Appl. No.: 476,757

[22] Filed: Mar. 18, 1983

[30] Foreign Application Priority Data

Mar. 19, 1982 [JP] Japan .................................. 57-45372

[51] Int. Cl.[4] .............................................. A61F 2/30
[52] U.S. Cl. ...................................... 623/18; 623/16
[58] Field of Search ..................... 3/1, 1.9, 1.91, 1.912,
3/1.911; 128/335, 92, 92 CA, 92 E, 92 G;
623/16, 17, 18, 19, 20, 21, 22, 23

[56] References Cited

U.S. PATENT DOCUMENTS

| 3,808,606 | 5/1974 | Tronzo | 3/1.9 |
| 4,051,598 | 10/1977 | Sneer | 3/1.9 |
| 4,156,943 | 6/1979 | Collier | 3/1.9 |

FOREIGN PATENT DOCUMENTS

| 2325585 | 11/1974 | Fed. Rep. of Germany | 3/1.912 |
| 2447787 | 4/1976 | Fed. Rep. of Germany | 3/1.9 |
| 2659591 | 7/1977 | Fed. Rep. of Germany | 3/1.9 |
| 2838335 | 3/1980 | Fed. Rep. of Germany | 3/1.9 |
| 2950536 | 7/1981 | Fed. Rep. of Germany | 3/1.912 |
| 2301217 | 7/1970 | France | 3/1.912 |
| 2025238 | 1/1980 | United Kingdom | 3/1.9 |

Primary Examiner—Richard J. Apley
Assistant Examiner—David J. Isabella
Attorney, Agent, or Firm—Sughrue, Mion, Zinn, Macpeak and Seas

[57] ABSTRACT

An artificial articulation includes a socket which has a spherical inner surface, a bone head ball member which is pivotably, slidably received in the spherical inner surface of the socket, and a stem which is connected to the ball head bone member. The socket is made of polycrystal alumina porcelain, the bone head ball member is made of dense silicon nitride porcelain, and the stem is made of either silicon nitride porcelain or partially stabilized zirconia porcelain. An outer surface of the stem and outer surface of the socket are coated with first and second cover layer.

17 Claims, 4 Drawing Figures

ARTIFICIAL ARTICULATION

BACKGROUND OF THE INVENTION

1. Field of the Invention

The present invention relates to an artificial articulation for replacing an articulation portion of a living body.

2. Description of the Prior Art

The function of an articulation of a living body can be damaged in an accident, such as in injuries resulting from a traffic accident, and can also be damaged by diseases, such as rheumatism, which cause bone to deform. When the articulation is damaged extensively and the chance of recovery is small, a replacement operation is effected to remove the articulation, and an artificial articulation is mounted in its place.

Such an artificial articulation is required to provide the following characteristics:

(1) Since it is to be embedded in a living body for a long period of time, the artificial articulation must have an affinity with the surrounding bone and tissue;

(2) The artificial articulation must not deteriorate and degenerate over time, and various characteristics of the artificial articulation, such as mechanical strength, should remain constant;

(3) The pivotal portion of the artificial articulation must be durable and must be able to reproduce the basic articulate function of the true articulation which it replaces;

(4) The artificial articulation must be innoxious to the living body.

The mechanical strength of the bone insertion portion of the artificial articulation is a particularly important factor because force, which is several times as large as the weight of a living body, may be applied to portions of the artificial articulation due to muscular strength acting on it, in addition to the weight of the living body. Thus, a high mechanical strength is required for the artificial articulation.

In a conventional artificial articulation, as shown in FIG. 1, a stem 4, which is made of nickel-chrome alloy stainless steel or cobalt-chrome-molybdenum alloy stainless steel and which is to be inserted into a bone B1, is connected to the bone head ball member 3 which is made of alumina porcelain. A socket 1, which is made of high-density polyethylene, is fixed by bone cement 2 in a hip-bone B2, and the bone head ball member 3 is pivotally, slidably connected to the socket 1. However, because the bone head ball member 3 which is made of alumina porcelain pivotally slides in the socket 1 which is made of high-density polyethylene, the inner surface of the socket 1 is worn by about 0.2 mm a year and must be replaced every three years. Further, although the metal stem 4 is connected to the bone B1 with bone cement 5 in order to prevent the stem from directly contacting the bone B1, a chemical reaction may take place between the bone cement 5 and the metal stem 4 when they are embedded in the bone B1 for a long period of time, and this reaction often injures the living body. An alternative method of using calcium phosphate rather than bone cement to connect the metal stem 4 to the bone B1 has not proven effective because of insufficient bonding strength between the calcium phosphate and the metal stem.

In addition, though alumina porcelain does not react with bone cement, an alumina porcelain stem is not very stong and is particularly weak in deflective strength when compared with the metal stem so that there is a risk of breakage when large stresses are placed on an alumina porcelain stem during movement of the living body.

SUMMARY OF THE INVENTION

The present invention is intended to eliminate the above-mentioned defects in the prior art artificial articulation. An object of the present invention is to provide an artificial articulation which does not adversely affect a living body and which is very resistant to wear.

The artificial articulation of the invention comprises a socket which consists essentially of polycrystal alumina porcelain, the socket having a spherical inner surface; a bone head ball member which consists essentially of dense silicon nitride porcelain, said ball member being pivotably, laterally received in said spherical inner surface of the socket; and a stem which consists essentially of a high-density silicon nitride porcelain or partially stabilized zirconia porcelain, the stem being connected to the bone head ball member. The bone head ball member and the stem can be integrally sintered, and an outer surface of the socket and the outer surface of the stem are porous, the size of the pores being between 20 $\mu$m and 500 $\mu$m.

In addition, when the stem consists essentially of partially stabilized zirconia porcelain, it is preferable to coat the outer surface of the stem and outer surface of the socket with first and second cover layers, the first cover layer being an oxidized alkaline-earth metal-phosphoric frit and the second layer being a calcium phosphate. It is further advantageous to make the surfaces of the first and second cover layer uneven by forming threads, longitudinal grooves, lateral grooves, corrugations, etc., on the surfaces.

DESCRIPTION OF THE PREFERRED EMBODIMENTS

Figure 1:
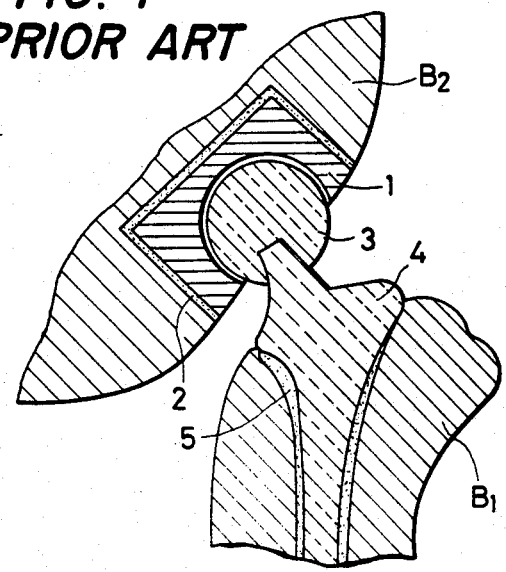
FIG. 1 is a longitudinal cross-sectional view of a conventional artificial articulation.
Figure 2:
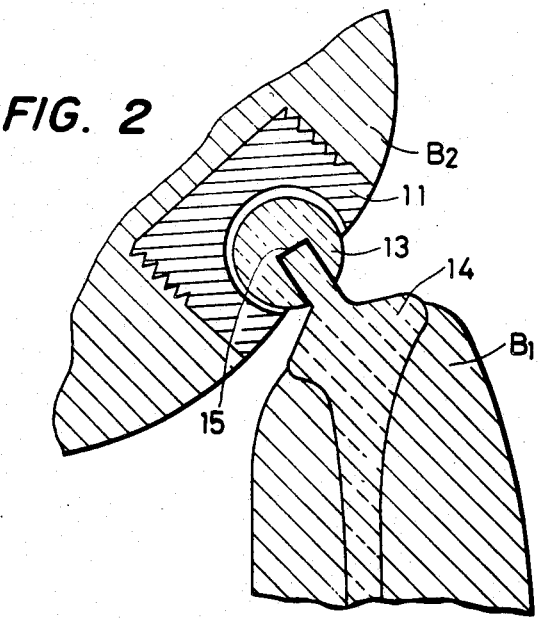
FIG. 2 is a longitudinal cross-sectional view of a first embodiment of an artificial articulation according to the present invention.

According to the embodiments of the present invention shown in FIG. 2, the artificial articulation comprises a socket 11 which is made of polycrystal alumina porcelain and which has a spherical inner surface; a bone head ball member 13 which is made of dense silicon nitride porcelain and which is pivotally, slidably received in the spherical inner surface of the socket 11; and a stem 14 which is made of high-density silicon nitride porcelain or partly stabilized $ZrO_2$ porcelain and which is connected to the bone head ball member 13.

The reason that the socket 11 is made of polycrystal alumina porcelain instead of high-density polyethylene and single crystal alumina, which have been used in the prior art, is that the polycrystal alumina porcelain is more resistant to wear and also wears uniformly in all directions. In addition, polycrystal alumina porcelain is compatible with other body members so that the socket 11, which is made of polycrystal alumina porcelain, can be threadedly connected directly to the bone by sewing an outer surface of the hip-bone B2 to the socket 11. Since the polycrystal alumina porcelain is compatible with other body members, no injury to living tissue results. The spherical inner surface of the socket 11, which is slidably coupled with the bone head ball member 13, is much more resistant to wear when compared with high-density polyethylene, and, therefore, the socket of the present invention does not need to be replaced nearly as often as prior art sockets.

Next, the bone head ball member 13 is made of high-density silicon nitride porcelain because this material has a very fine fibrous structure and very high mechanical strength. In addition, its bending strength is beyond 100 kg/mm$^2$ and, in fact, is about 150 kg/mm$^2$. Accordingly, since there is little risk of breakage, the diameter of the ball member 13 may be reduced to 22 mm, while conventional ball members are required to be 26 mm in diameter. Reducing the size of the socket reduces the expense of producing the artificial articulation. In addition, the reduced size also minimizes the burden for the living body, and, because the polycrystal alumina porcelain of the socket 11 and the silicon nitride porcelain of the bone head ball member 13 are extremely resistant to wear due to their fibrous organization, the replacement period for the artificial articulation is lengthened, and the amount of harmful abrasion powder generated is reduced. Further, it has been found through biological tests that the artificial articulation of the present invention is well accepted by the living body and facilitates bone formation.

The reason that the stem 14 is made of high-density silicon nitride porcelain or partially stabilized zirconia porcelain is that the stem is required to have a high mechanical strength. Alumina porcelain and stabilized zirconia porcelain are low in mechanical strength and may be easily broken. Further, the metal stem is often not compatible with the living body, and injury results in spite of the high strength of the metal stem. According to the present invention, those defects in the prior art have been overcome by using high-density silicon nitride porcelain which has a bending strength between 50 kg/mm$^2$ and 150 kg/mm$^2$, or by using partially stabilized zirconia porcelain which has a bending strength between 70 kg/mm$^2$ and 150 kg/mm$^2$.

Further, since both the bone head ball 13 and the stem 14 are made of a silicon nitride material, it is preferable to produce them simultaneously and integrally into a single body. It is even more preferable to make the outer surface of the socket 11 and the stem 14 porous by forming pores having a size between 20 μm and 500 μm within these elements so that they will be accepted by and strongly bonded to the living body.

An embodiment of the method of producing the artificial articulation of the first embodiment of the presention invention will now be described. A circular cylinder which has a diameter of 40.8 mm and a length of 36 mm was made by a known method using a blank consisting of high-plurality Al$_2$O$_3$ by 98 weight % (hereinafter, the word "weight" is omitted), MgO of 1% and CaO of 1%, all available on the market. Then, a semi-spherical recess which has a diameter of 26.4 mm was formed in the central portion of one of the ends of the circular cylinder. The circular cylinder was sintered at 1700° C. for 30 minutes to produce the socket 11, after the circular cylinder had been threaded with a pitch of 1 mm at its circumferential side surface portion which was located adjacent to its other end, and slip was applied. The slip included, in addition to the same blank as the circular cylinder, 20% carbon powder which has a diameter of 22 μm at the entire outer surface, except for the semi-spherical recessed portion. In the socket thus produced, the specific gravity was 3.92; the crystal particle size was 4 μm on the average; and the surface, except for the semi-spherical recessed portion, contained a number of pores of 90 μm in a surface layer which was 0.5 mm thick.

Next, a ball which has a diameter of 25.2 mm and which contains a recessed portion 15, as shown in FIG. 2, was formed by a rubber press using a powder which contains 5% Y$_2$O$_3$, in addition to α-Si$_3$N$_4$ powder which has an average particle size of 2 μm, both available on the market. Further, by using the same powder an integral member, including a stem 14, was formed by a rubber press. After the surface of the stem had been applied to a thickness of 0.5 mm with slip of the same powder of silicon nitride containing 20% carbon powder which has a 100 μm particle size, an integral ball and stem member were produced after 30 minutes of burning. On the other hand, with respect to the stem comprised of partially stabilized zirconia, by burning a powder which contains 2 mole-% Y$_2$O$_3$ at 1550° C., in addition to pure ZrO$_2$, a stem of partially stabilized ZrO$_2$ was produced. The stabilized ZrO$_2$ includes about 80% tetragonal crystal system ZrO$_2$ and about 10% of monoclinic crystal system ZrO$_2$ and has a bending strength of about 130 Kg/mm$^2$, which is about 2~3 times as strong as the conventional alumina porcelain. The surface was made porous in the same manner as the alumina porcelain and the silicon nitride porcelain. The stem can then be fixedly connected to the bone head ball by an expansion fit by inserting the stem into the recessed portion 15 of the bone head ball after the stem has been cooled at −60° C. Even if the stem is connected to the bone head ball with a bonding material such as polyethylene, the bonding material provides little injury to the living body and causes no substantial problems.

Figure 3:
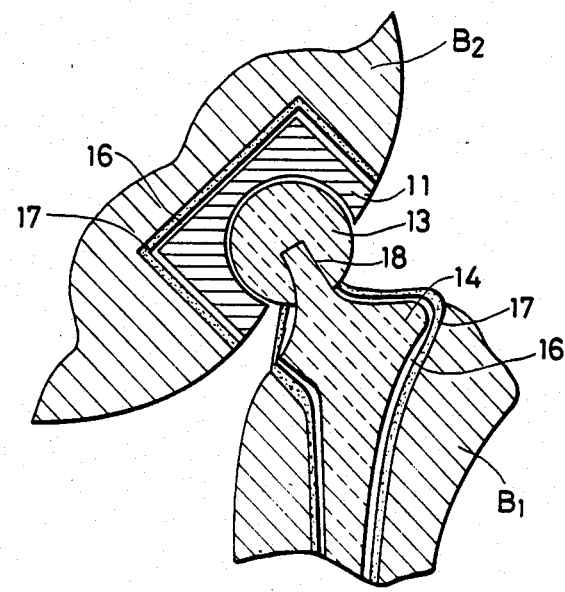
FIGS. 3 and 4 are longitudinal cross-sectional views of further embodiments of an artificial articulation according to the present invention.

According to a second embodiment of the present invention shown in FIG. 3, a first cover layer 16 made of frit composed of oxidized alkaline-earth metals, a metallic oxide and phosphoric acid anhydride is provided over the outer surface of the stem 14 and the outer surface of the socket 11, the metallic oxide being an oxide of at least one metal selected from the group consisting of Zn, Al, Si, B, Ti, Fe and alkaline metals. In addition, a second cover layer 17 made of calcium phosphate is provided over the first cover layer 16.

When the stem is made of partially stabilized zirconia porcelain, it is particularly advantageous to provide the cover layer 16 over the surface of the zirconia porcelain zince zirconia porcelain does not adhere well to the bone B1. The first layer, made of the above-mentioned frit, has a strong adhesive force with the partially stablized porcelain. The second layer, made of calcium phosphate, is provided over the first layer since the second layer is more compatible with a living body when in contact therewith than is the first layer.

The frit constituting the first layer contains, as its essential components, oxidized alkaline earth metals and phosphoric acid anhydride and may further contain an oxide of at least one kind of metal selected from Zn, Al, Si, B, Ti, Fe and alkaline metals. The optimal composition of the frit are disclosed in Japanese Utility Model Application Laid-open No. 140756/SHO-55(1980) (correspond to U.S. Pat. No. 4,308,064), the disclosure of which is incorporated herein by reference, and the composition of the frit is hereinafter referred to as "A". Various frit compositions "A" are shown in TABLE 1 with their corresponding characteristics.

TABLE 1

| FRIT NO. | COMPOSITION (MOL %) (OXIDE OF FOLLOWING ROW OF ELEMENTS) | | | | | | | | | | | | Transient Point °C | Coefficient of Linear Expansion × $10^{-7}$/°C. |
|---|---|---|---|---|---|---|---|---|---|---|---|---|---|---|
| | P | Ba | Ca | Mg | Zn | Al | Si | B | Ti | Fe | Na | K | | |
| 1 | 46 | 32 | 20 | | | 2 | | | | | | | 525 | 120 |
| 2 | 46 | 47 | | 7 | | | | | | | | | 525 | 150 |
| 3 | 47 | | 44 | | 9 | | | | | | | | 507 | 130 |
| 4 | 60 | 20 | 5 | 5 | | 5 | | | | | | 5 | 510 | 100 |
| 5 | 43 | 3 | 41 | 2 | | | 1 | | | 11 | | | 505 | 102 |
| 6 | 47 | 3 | 49 | | | | | 1 | | | | | 535 | 120 |
| 7 | 70 | 10 | | 10 | 5 | 5 | | | | | | | 640 | 80 |
| 8 | 70 | 10 | | 20 | | | | | | | | | 560 | 78 |
| 9 | 60 | 20 | | | 20 | | | | | | | | 530 | 100 |
| 10 | 45 | 15 | 20 | | | | | | | | | 20 | 520 | 112 |
| 11 | 45 | 15 | 20 | | | | | | | | 20 | | 515 | 120 |
| 12 | 60 | 15 | | 5 | 5 | 9 | 1 | | | | | 5 | 520 | 93 |
| 13 | 50 | 37 | | 3 | | 2 | 8 | | | | | | 490 | 130 |
| 14 | 45 | 30 | 15 | | | 2 | 1 | 5 | 1 | 1 | | | 510 | 128 |
| 15 | 47 | 2.5 | 49.5 | | | | 1 | | | | | | 520 | 114 |
| 16 | 46 | 47 | | 5 | | 2 | | | | | | | 488 | 150 |
| 17 | 47 | 7.5 | 44.5 | | | | 2 | | | | | | 498 | 122 |
| 18 | 46 | 12 | 40 | | | 2 | | | | | | | 513 | 121 |

The optimum composition of the calcium phosphate has a Ca/P ratio between 1.4 and 1.75, and tricalcium phosphate $Ca_3(PO_4)_2$ and hydroxy apatite $Ca_{10}(PO_4)_6(OH)_2$ are particularly preferable. The composition of the calcium phosphate is hereinafter referred to as "B". The second cover layer 17 may also include a suitable frit to enhance the sintering performance and the mechanical strength of the "B" composition. For example, 0.5 to 15 weight % of the "A" composition may be added to 85-99.5 weight % of the "B" composition, the composite composition being referred to as "C". In addition, it has been found desirable to add 3-23 weight % of $Y_2O_3$ to 77-97 weight % of the "C" composition. The resultant composition has high mechanical strength and also has a coefficient of thermal expansion within a range of 90-160×10-7/°C., as described in the above-mentioned Japanese Utility Model Application Laid-open No. 140756/SHO-55(1980) and another Japanese Utility Model Application Laid-open No. 80771/SHO-55 (1980) (these two applications were combined and correspond to U.S. Pat. No. 4,308,064). The disclosure of this latter Japanese Utility model is also enclosed herewith by reference. The sintering temperature of the second layer is preferably selected to be between 800° and 1200° C.

An example of this embodiment will now be described. A cylindrical column having a diameter of 36.8 mm and a length of 32 mm was made in the known manner by using a body containing 98 weight % of high purity $Al_2O_3$, 1 weight % of MgO and 1 weight % of CaO, all the materials being available on the market. The column was formed with a semi-spherical recess at a central portion in its bottom surface and baked at 1600° C. for 60 minutes to produce a socket 11. Next, $H_3PO_4$, $BaCO_3$, $CaCO_3$, $MgCO_3$, $Na_2CO_3$, and $SiO_2$, all available on the market, were measured and sized with a weight ratio such that the composition of the mixture after baking became that of the frit No. 5 shown in TABLE 1. The mixture was then baked into a molten state at 1300° C. for 2 hours. The molten mixture was then rapidly cooled with water to obtain the frit No. 5. The frit No. 5 was crushed into powder by a trommel until 40% of the powder contained particles having a size of 5 μm or less. A part of the powder was put into solution in which 1% of methyl cellulose was dissolved with respect to 100% of the powder and agitated to obtain slip. The slip was applied over the outer surface of the socket 11 with a thickness of 0.5 mm and then baked, after being dried, at 700° C. in the atmosphere to obtain the first cover layer 16. Then the remainder part of the frit No. 5 powder was mixed with hydroxy apatite of average particle diameter of 0.1 μm available on the market in a wet state in alcohol to form slip, the weight % of the frit No. 5 powder being 5 and the weight % of the hydroxy apatite being 95. The slip was applied over the surface of the first cover layer and then baked, after being dried, at 900° C. in the atmosphere for 40 minutes to obtain the second cover layer 17.

A ball having a diameter of 21.2 mm was formed by a rubber press method by using a body obtained by adding 5% of $Y_2O_3$ to α-$Si_3N_4$ having an average particle diameter of 2 μm, available on the market. The ball was then formed with a cylindrical recess having a diameter of 5 mm and a depth of 8 mm and baked at 1700° C. in an atmosphere of nitrogen for 30 minutes to obtain the bone head ball member 13. In addition, a pattern of the stem 14 was formed by a rubber press method by using a body obtained by adding 4 mol % of $Y_2O_3$ to pure $ZrO_2$, and the pattern of the stem was baked at 1550° C. for 60 minutes to obtain the stem 14 made of partially stablized $ZrO_2$ containing about 80% of tetragonal system $ZrO_2$ and about 20% of cubic system $ZrO_2$. The thus-obtained stem had a deflective strength of about 130 kg/mm². This deflective strength is about two or three times as large as that of conventional alumina porcelain. First and second cover layers were formed over the surface of the stem in the same manner as they were formed on the outer surface of the socket as described above. The zirconia stem and bone head ball member may be fixedly connected to each other by expansion fit, that is for example, by inserting the stem into the recess 18 in the bone head ball member after the stem has been cooled to 60° C. below zero. Alternatively, these members may be bonded with a binding agent such as polyethylene without causing any substantial problem in adhesive strength.

Figure 4:
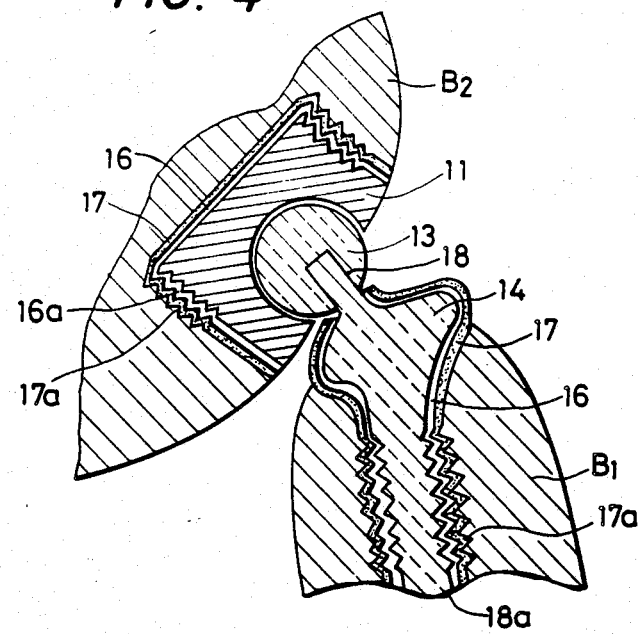

It is preferable to make the surface of each of the first and second cover layers uneven by forming threads, longitudinal grooves, lateral grooves, corrugations, etc., on these surfaces to enhance the bonding strength between the artificial bone and each of the living body bones $B_1$ and $B_2$. In the above-mentioned embodiment, the first and second cover layers had a flat surface. FIG. 4 shows an embodiment in which threads are provided. Although the second cover layer, which is made of calcium phosphate as its main component, has good affinity with the living body bones $B_1$ and $B_2$, if powder such as burnt carbon particles or organic materials having a diameter between 20 and 500 μm is added to the slip for forming the second cover layer before the slip is applied onto the surface of the first cover layer, pores having a size between 20 and 500 μm may be formed after baking to thereby further enhance the affinity. Further, if the composition of each of the first and second layers is suitably selected so that their sintering temperatures are identical, the first and second layers may be simultaneously baked at 700° to 1200° C. Alternatively, the layers may be deposited by a well-known method such as chemical vapor deposition or physical vapor deposition.

As described above, the artificial articulation according to the present invention does not adversely affect a living body and is very resistant to wear. It also has a high mechanical strength and adheres very well with a living body.

We claim:

1. A biocompatible artificial articulation prosthesis including an acetabular socket consisting essentially of polycrystal alumina porcelain wherein said socket having formed therein a special inner surface to be pivotally coupled to with a femoral ball member, said femoral member consisting essentially of dense silicon nutride porcelain;

a stem adapted to be inserted into a prepared medullary cavity and being connected to, at one end thereof, said femoral ball member, said stem consisting of partially stabilized zirconia porcelain;

said prosthesis further including a first layer disposed over an outer surface of said stem and an outer surface of said socket and a second layer disposed over said first layer wherein said first layer and second layer consist essentially of oxidized alkaline metal-phosphoric and anhydride frit and calcium phosphate, respectively.

2. The artificial articulation as claimed in claim 1, wherein said bone head ball member and said stem are integrally sintered.

3. The artificial articulation as claimed in claim 1, wherein the outer surface of said socket not including said spherical inner surface is porous with pores having a size between 20 μm and 500 μm.

4. The artificial articulation as claimed in claim 2, wherein an outer surface of said socket not including said spherical inner surface is porous with pores having a size between 20 μm and 500 μm.

5. The artificial articulation according to claim 3, wherein an outer surface of said stem is porous with pores having a size between 20 μm and 500 μm.

6. The artificial articulation according to claim 4, wherein an outer surface of said stem is porous with pores having a size between 20 μm and 500 μm.

7. The artificial articulation as claimed in claim 1 wherein said partially stabilized zirconia porcelain has a bending strength between 70 and 150 kg/mm$^2$.

8. The artificial articulation as claimed in claim 1 wherein said first cover layer further includes an oxide of at least one metal selected from the group consisting of Zn, Al, Si, B, Ti, Fe and alkaline metals.

9. The artificial articulation as claimed in claim 1 wherein said calcium phosphate has a Ca/P ratio between 1.4 and 1.75.

10. the artificial articulation as claimed in claim 1 wherein said calcium phosphate is either tricalcium phosphate or hydroxy apatite.

11. The artificial articulation as claimed in claim 1 wherein said second layer is formed by mixing between 85 and 99.5 weight % of said calcium phosphate with between 0.5 and 15 weight % of said first covered layer.

12. The artificial articulation as claimed in claim 11 wherein said second layer is further formed by mixing between 77 and 95 weight % of said calcium phosphate-first layer mixture with between 3 and 23 weight % of $Y_2O_3$.

13. The artificial articulation as claimed in claim 1 wherein said second cover layer has an uneven surface.

14. The artificial articulation as claimed in claim 1 wherein said second layer has pores between 20 and 500 μm.

15. The artificial articulation as claimed in claim 1, wherein said oxidized alkaline earth metal-phosphoric frit is calcium phosphate frit.

16. The artificial articulation as claimed in claim 15 wherein a Ca/P atom ratio of said calcium phosphate frit is between 0.2 and 0.75.

17. The artificial articulation as claimed in claim 1 wherein outer surfaces of said first and second cover layers are made uneven by forming either threads, longitudinal grooves, lateral grooves, or corrugations on these surfaces.

* * * * *